(12) United States Patent
Matthison-Hansen (10) Patent No.: US 11,937,781 B2
(45) Date of Patent: Mar. 26, 2024

(54) ENDOSCOPE COMPRISING AN ARTICULATED BENDING SECTION BODY

(71) Applicant: AMBU A/S, Ballerup (DK)

(72) Inventor: Kaspar Mat Matthison-Hansen, Helsingør (DK)

(73) Assignee: AMBU A/S, Ballerup (DK)

( * ) Notice: Subject to any disclaimer, the term of this patent is extended or adjusted under 35 U.S.C. 154(b) by 66 days.

(21) Appl. No.: 17/344,526

(22) Filed: Jun. 10, 2021

(65) Prior Publication Data

US 2021/0393113 A1    Dec. 23, 2021

(30) Foreign Application Priority Data

Jun. 19, 2020   (EP) .................................... 20181064

(51) Int. Cl.
*A61B 1/005* (2006.01)
*A61B 1/00* (2006.01)
(Continued)

(52) U.S. Cl.
CPC .......... *A61B 1/0055* (2013.01); *A61B 1/0057* (2013.01); *A61B 1/008* (2013.01); *A61B 1/012* (2013.01); *A61B 1/00045* (2013.01)

(58) Field of Classification Search
CPC . A61B 1/00071; A61B 1/0055; A61B 1/0057; A61B 1/008; A61B 1/012; A61B 1/018
See application file for complete search history.

(56) References Cited

U.S. PATENT DOCUMENTS

| 4,580,551 A | 4/1986 | Siegmund et al. |
| 4,651,718 A | 3/1987 | Collins et al. |
| (Continued) | | |

FOREIGN PATENT DOCUMENTS

| CN | 103228199 A | 7/2013 |
| DE | 19815598 | 10/1999 |
| (Continued) | | |

OTHER PUBLICATIONS

ESR in European Application No. 21179386.4, dated Nov. 8, 2021, 7 pgs.
(Continued)

*Primary Examiner* — Aaron B Fairchild
(74) *Attorney, Agent, or Firm* — Faegre Drinker Biddle & Reath LLP (57) ABSTRACT

An articulated bending section body has a number of segments including a proximal end segment, a distal end segment and a number of intermediate segments. Each intermediate segment has a central passage adapted in cross-sectional shape to receive and support the exterior surface of a bendable tubular member providing a working channel of the endoscope. The cross-sectional shape includes a number of sectors of a circular periphery having a shared center and the same radius, the total length of the sectors being longer than half of the circular periphery. The cross-sectional shape comprises at least one outwardly extending lobe. The exterior surface of the bendable tubular member providing the working channel of the endoscope forms a closed lumen adjacent but separated from the working channel of the endoscope.

20 Claims, 8 Drawing Sheets

(51) Int. Cl.
*A61B 1/008* (2006.01)
*A61B 1/012* (2006.01)

(56) References Cited

U.S. PATENT DOCUMENTS

| | | |
|---|---|---|
| 4,706,653 A | 11/1987 | Yamamoto |
| 4,745,470 A | 5/1988 | Yabe et al. |
| 4,778,247 A | 10/1988 | Carpenter |
| 4,796,607 A * | 1/1989 | Allred, III ........... A61B 1/0057 138/120 |
| 4,832,003 A | 5/1989 | Yabe |
| 4,856,495 A | 8/1989 | Tohjoh et al. |
| 4,860,732 A | 8/1989 | Hasegawa et al. |
| 4,911,148 A | 3/1990 | Sosnowski et al. |
| 4,918,521 A | 4/1990 | Yabe et al. |
| 5,089,895 A | 2/1992 | Fraker et al. |
| 5,325,845 A | 7/1994 | Adair |
| 5,376,960 A | 12/1994 | Wurster |
| 5,379,756 A | 1/1995 | Pileski et al. |
| 5,418,566 A | 5/1995 | Kameishi |
| 5,438,975 A | 8/1995 | Miyagi et al. |
| 5,547,457 A | 8/1996 | Tsuyuki et al. |
| 5,830,401 A | 11/1998 | Prichard et al. |
| 5,928,136 A | 7/1999 | Barry |
| 5,966,168 A | 10/1999 | Miyazaki |
| 6,004,263 A | 12/1999 | Nakaichi et al. |
| 6,110,104 A | 8/2000 | Suzuki et al. |
| 6,302,616 B1 | 10/2001 | Takahashi |
| 6,456,863 B1 | 9/2002 | Levin et al. |
| 6,554,793 B1 | 4/2003 | Pauker et al. |
| 7,455,806 B2 | 11/2008 | Junger et al. |
| 7,758,495 B2 | 7/2010 | Pease et al. |
| 8,182,422 B2 | 5/2012 | Bayer et al. |
| 8,547,424 B2 | 10/2013 | Ishii et al. |
| 8,790,250 B2 | 7/2014 | Petersen et al. |
| 9,125,582 B2 | 9/2015 | Petersen |
| 9,220,400 B2 | 12/2015 | Petersen |
| 9,486,595 B2 | 11/2016 | Borrye et al. |
| 9,572,482 B2 | 2/2017 | Lin |
| 9,622,649 B2 | 4/2017 | Lin |
| 2002/0022765 A1 | 2/2002 | Belson |
| 2002/0055668 A1 | 5/2002 | Pauker |
| 2003/0056540 A1 | 3/2003 | Mukasa et al. |
| 2004/0044270 A1* | 3/2004 | Barry ................ A61B 1/0056 600/142 |
| 2004/0199052 A1 | 10/2004 | Banik et al. |
| 2004/0242963 A1 | 12/2004 | Matsumoto et al. |
| 2005/0070759 A1 | 3/2005 | Armstrong |
| 2005/0075538 A1 | 4/2005 | Banik et al. |
| 2005/0119527 A1 | 6/2005 | Banik et al. |
| 2005/0131279 A1 | 6/2005 | Boulais et al. |
| 2005/0140068 A1 | 6/2005 | Junger et al. |
| 2005/0154262 A1 | 7/2005 | Banik et al. |
| 2005/0203341 A1 | 9/2005 | Welker et al. |
| 2005/0234499 A1 | 10/2005 | Olson et al. |
| 2006/0178556 A1 | 8/2006 | Hasser et al. |
| 2007/0129466 A1 | 6/2007 | Kagawa et al. |
| 2007/0249896 A1 | 10/2007 | Goldfarb et al. |
| 2007/0249907 A1 | 10/2007 | Boulais et al. |
| 2008/0221393 A1 | 9/2008 | Padget et al. |
| 2008/0249483 A1 | 10/2008 | Slenker et al. |
| 2008/0268559 A1 | 10/2008 | Jung |
| 2008/0287741 A1 | 11/2008 | Ostrovsky et al. |
| 2009/0054728 A1 | 2/2009 | Trusty |
| 2009/0177040 A1 | 7/2009 | Lyons et al. |
| 2009/0209819 A1 | 8/2009 | Kitagawa et al. |
| 2010/0210905 A1 | 8/2010 | Takeuchi et al. |
| 2010/0217082 A1 | 8/2010 | Ito et al. |
| 2010/0280316 A1 | 11/2010 | Dietz et al. |
| 2010/0324367 A1 | 12/2010 | Matsumoto et al. |
| 2011/0251519 A1 | 10/2011 | Romoscanu |
| 2012/0002981 A1 | 1/2012 | Park |
| 2012/0165608 A1 | 6/2012 | Banik et al. |
| 2014/0024898 A1* | 1/2014 | Konstorum ........ A61B 1/00071 600/142 |
| 2015/0366436 A1 | 12/2015 | Henrik |
| 2016/0101254 A1 | 4/2016 | Hansen et al. |
| 2021/0137354 A1 | 5/2021 | Bob et al. |

FOREIGN PATENT DOCUMENTS

| | | |
|---|---|---|
| DE | 10010931 | 9/2001 |
| DE | 102018110620 A1 | 11/2019 |
| JP | 2005-152043 A | 6/2005 |
| KR | 10-2012-0056363 A | 6/2012 |
| WO | 2007/124211 A2 | 11/2007 |
| WO | 2009/100368 A1 | 8/2009 |
| WO | 2010/066787 A1 | 6/2010 |
| WO | 2010/066788 A2 | 6/2010 |
| WO | 2010/066789 A1 | 6/2010 |
| WO | 2010/066790 A1 | 6/2010 |
| WO | 2010/067765 A1 | 6/2010 |
| WO | 2014/106510 A1 | 7/2014 |
| WO | 2014/106511 A1 | 7/2014 |
| WO | 2016/188537 A1 | 12/2016 |
| WO | 2016/188538 A1 | 12/2016 |
| WO | 2016/188539 A1 | 12/2016 |
| WO | 2016/188540 A1 | 12/2016 |
| WO | 2016/188541 A1 | 12/2016 |
| WO | 2016/188542 A1 | 12/2016 |
| WO | 2016/188543 A1 | 12/2016 |
| WO | 2018/059643 A1 | 4/2018 |

OTHER PUBLICATIONS

European Search Report and Search Opinion Received for EP Application No. 20181064.5, dated Nov. 20, 2020, 7 pages.

* cited by examiner

ENDOSCOPE COMPRISING AN ARTICULATED BENDING SECTION BODY

CROSS-REFERENCE TO RELATED APPLICATIONS

This application claims the benefit of and priority from European Patent Application No. 20181064.5, filed Jun. 19, 2020, which is incorporated herein by reference in its entirety.

TECHNICAL FIELD

The present disclosure relates to insertion endoscopes, in particular to the articulated bending section of such an endoscope.

BACKGROUND

Insertion endoscopes typically comprises a handle at the proximal end to be gripped by an operator and a flexible elongated insertion tube terminated at the distal end in a tip part at the end of a highly bendable, e.g. articulated, bending section, controllable by the operator. The tip part normally comprises a visual inspection means such as a camera, and illumination means such as LED's or exit apertures of light fibers and whatever optics is needed in that connection. Electrical wiring for the camera and other electronics such as the LED lighting run along the inside of the elongated insertion tube from the handle to the tip at the distal end. When, as mentioned, the illumination is instead fiber-optic, the optical fibers run along inside of the elongated insertion tube.

Thus, the controllable bending section is normally an articulated section at the distal tip of the elongated insertion tube that can be controlled by the operator via control knobs arranged on the handle. Typically, this control is effected by tensioning or slacking pull wires also running along the inside of the elongated insertion tube from the articulated tip part to a control mechanism of the handle. Furthermore, a working channel may run along the inside of the elongated insertion tube from the handle to the tip, e.g. allowing liquid to be removed from the body cavity or allowing the insertion of surgical instruments or the like into the body cavity.

Thus, using the controls allows the operator to advance the distal tip of the endoscope to a desired location by means of a series of actions involving inter alia bending the bending section in a desired direction, advancing the elongated insertion tube and turning the elongated insertion tube by turning the handle which is rigidly connected thereto. Navigating a tortuous path of bends and turns to a location of interest may subject the elongated insertion tube including the distal controllable bending section to substantial forces including compression, torsion, and bending. The main body of the elongated insertion tube is essentially only bendable enough to follow the direction taken by the articulated bending section. In fact, it could be said that it is an essential part of the purpose of the elongated insertion tube to transmit the longitudinal pushing forces and rotary torsional forces from the handle to the distal end of the elongated insertion tube in order to allow these maneuvers.

It is well known to provide the articulated bending section using a molded single-piece ending section body comprising a distal end segment forming the tip part of the endoscope for accommodating the camera etc. as explained initially, a proximal end segment for connection to the elongated insertion tube body, and a number of more or less identical articulated intermediate segments. The single piece bending section body is a generally elongate cylindrical member, i.e. cylindrical save for the cut-outs between the segments allowing the bending section to bend. In other words, geometrically seen the cylindrical outer surfaces of the segments share the same cylindrical envelope. An example of such a molded single-piece bending section body is found in WO2014/106511, incorporated herein by reference.

The articulation of the segments, including the proximal end segment, the intermediate segments and the distal end segment is provided by hinge members, in WO2014/106511 formed as foil hinges between segments, a foil hinge being a short strip of material so thin that it allows the material to bend in an elastic manner between two segments.

In WO2014/106511 the foil hinges between adjacent segments are split in three across the diameter of the generally cylindrical bending section body, one somewhat centrally arranged hinge part and two peripheral hinge parts diametrically opposite each other close to the external periphery of the geometrical envelope of the bending section body. The somewhat centrally arranged hinge part together with one of the peripheral hinge parts, abut and supports an inner tube forming the working channel against kinking between the segments.

The molded single-piece bending section body of WO2014/106511 has shown quite successful in practice. It has been found that some improvements with respect to the above-mentioned rotary torsional forces may be possible. In this respect, the centrally arranged hinge part only has a relatively smaller effect on the resistance to torsion, as the majority of the torsional forces are being taken up by the peripheral hinge parts. Moreover, having a centrally arranged hinge part will inevitably limit the maximum possible diameter of a tube forming the working channel.

SUMMARY

Is the object of the present disclosure to provide an endoscope with a bending section body that overcomes the above issues and allows for a good utilization of the limited space across the diameter of the bending section body.

According to a first aspect of the disclosure, this object is achieved by an endoscope comprising an articulated bending section body, said articulated bending section body comprising number of segments including a proximal end segment, a distal end segment and a number of intermediate segments arranged between the proximal segment and the distal segment, where a pair of end hinge members is provided between the proximal end segment and one of said intermediate segments, where a pair of end hinge members is provided between the distal end segment and one of said intermediate segments, and where a pair of intermediate hinge members is provided between any adjacent intermediate segments, at least some of said intermediate hinge members defining a longitudinal central plane of said articulated bending section body, where each intermediate segment has a central passage adapted in cross-sectional shape to receive and support the exterior of a bendable tubular member providing a working channel of the endoscope, where the cross-sectional shape comprises a number of sectors of a circular periphery having a shared center and the same radius, the total length of said sectors being longer than half of said circular periphery, so as to provide said support for the exterior of the bendable tubular member providing the working channel of the endoscope, and where said cross-sectional shape comprises at least one outwardly extending lobe, wherein the exterior of the bendable tubular member providing the working channel of the endoscope forms a closed lumen adjacent but separated from the working channel of the endoscope.

Thereby, a good utilization of the limited space available is provided. At the same time the width of the peripheral hinge parts may be made wider in the diametrical direction without reducing the diameter of the tube forming the working channel, in turn increasing the resistance to torsional forces.

According to a preferred embodiment of the first aspect of the disclosure said intermediate segments are symmetrical about said longitudinal central plane. By arranging the central aperture with the lobes in a symmetrical manner, thereby making the segments symmetrical, it becomes possible to arrange electrical cables, optical light fibers etc. centrally, so as to avoid unnecessary strain during bending. Conversely, it also becomes possible to arrange pull-wires where maximum force pulling force, and hence bending force on the bending section can be achieved.

Alternatively, according to another preferred embodiment of the first aspect of the disclosure, said shared center lies in the longitudinal central plane and said at least one lobe is arranged asymmetrical with respect to said longitudinal central plane. This allows space for the electrical cables, optical fiber, etc without conflicting with the hinges.

According to a further preferred embodiment of the first aspect of the disclosure, a pair of lobes are arranged symmetrically about said longitudinal central plane, and pull wires are arranged in the closed lumens formed adjacent but separated from the working channel of the endoscope. By this arrangement space is saved because a partitioning wall in the bending section body itself, between the pull-wires and the tube forming the working channel can be avoided. Thus, the working channel tube may have a larger diameter.

According to another embodiment a cable conduit is accommodated in said closed lumen. This cable conduit may keep the electrical cables optical fibers etc. well bundled, in particular between the segments, while also serve to support the tube forming the working channel, in the sectors where it is not supported by the central passage.

According to a further embodiment, the tubular member delimits the pull wire aperture thereby keeping the pull wire in the pull wire aperture.

According to yet a further embodiment, an outer diameter of the articulated bending section is below 3.0 mm, preferably below 2.8 mm. This makes the disposable endoscope suitable for narrow passages, allowing it to be used as e.g. a bronchoscope or an ureteroscope.

According to another embodiment, the disclosure allows for an inner diameter of the working channel of at least 1.2 mm, preferably at least 1.3 mm. This in turn makes the disposable endoscope suitable for a wider range of insertable tools.

According to a second aspect of the disclosure the object is solved by a system comprising a display unit and an endoscope according to the first aspect of the disclosure connectable to said display unit.

BRIEF DESCRIPTION OF THE DRAWINGS

The disclosure will now be made in greater detail based on non-limiting exemplary embodiments and the drawings on which.

DETAILED DESCRIPTION

Figure 1:
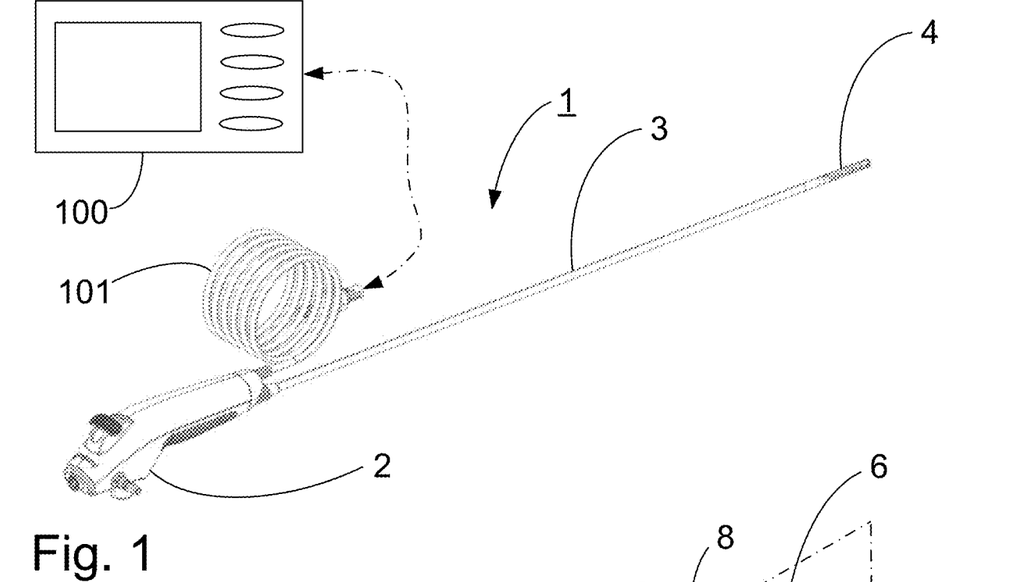
FIG. 1 shows a system comprising a display unit and an endoscope.

Turning first to FIG. 1 a system comprising a display device 100 and an endoscope 1 connectable to the display device 100 by means of a cable 101 or a wireless connection is shown. The endoscope 1 comprises a handle 2 at the proximal end and an insertion tube 3 connected to a bending section 4 forming part of the distal end of the endoscope 1. The bending section 4 comprises an articulated bending section body 5. The bending section body 5 is not visible in FIG. 1 because it is covered by a thin external sheath. Reference is therefore now made to FIGS. 2 to 15.

The bending section body has a number of segments including a proximal end segment 6, a distal end segment 7 and intermediate segments 8 arranged between the proximal segment and the distal segment, and hinges 18a, 18b connecting adjacent of the segments, at least some of the hinges defining a longitudinal bending plane S (see FIGS. 7 and 9) of the bending section body 5. The bending section body 5 is preferably integrally molded as one single-piece item in a suitable molding process, such as injection molding, together with the hinge members connecting the segments to each other. Each intermediate segment has a wall 9 with a central passage 12 having a cross-section shape including a bendable tube support sector 15 connected to a lobe sector 16, the bendable tube support sector having a periphery connected to a periphery of the lobe sector. The periphery of the bendable tube and the periphery of the lobe sector define a closed lumen 12' of the central passage 12. The longitudinal bending plane S traverses the bendable tube support sector and the lobe sector.

The periphery of the bendable tube support sector can be defined by one or more arcuate sections and has an arc length (the arc defined by the combined one or more arcuate sections) corresponding to an arc greater than 220 degrees, preferably about 270 degrees. If more than one arcuate section defines the periphery of the bendable tube support sector, the sum of their lengths comprises the length of the periphery of the bendable tube support sector. The wall comprises opposite protrusions defining a gap intermediate the bendable tube support sector and the lobe sector. The gap is formed between opposite surfaces of the periphery of the central passage and is narrower than a diameter of the bendable tube. The central passage is devoid of material across the gap, such that the space defined by the bendable tube support sector along a plane traversing the wall is contiguous with the space defined by the lobe sector along said plane.

The arcuate sections each has an arcuate length, a radius, and a center C, the number of arcuate sections adapted to receive a bendable tube 14, or bendable tube member, having an outer circumference 13 and providing the working channel 14' of the endoscope, a sum of the arcuate lengths of the arcuate sections being longer than half of the outer circumference of the bendable tube so as to support the bendable tube against outward deformation. The arcuate sections are sized and shaped to match the cross-section shape of the bendable tube. The bendable tube may have a cylindrical shape in which case the arcuate sections have a common radius and center. The bendable tube may have an oval shape in which case the arcuate sections do not have a common radius but have a common center. The sum can comprise contiguous arcuate sections and sections that are not contiguous, as shown in FIGS. 9-11 and 14.

The periphery of an arcuate section of the bendable tube support sector can be defined as a plurality of adjacent or contiguous arcs having a common center. In other words, if the bendable tube support sector has a substantially circular periphery, the plurality of adjacent or contiguous arcs having a common center define a portion of the circle. The common center of the arcs lies in the longitudinal bending plane. The plurality of arcs have a common radius if the periphery is substantially circular but different radii otherwise.

Figure 10:
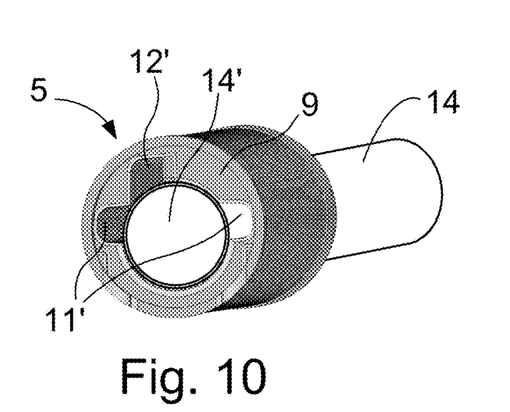
FIG. 10 presents a perspective distal end view of the bending section body of FIG. 9, showing the central passage with a cross-section shape including a bendable tube support sector connected to a lobe sector, with the bendable tube extending through the bendable tube support sector.
Figure 11:
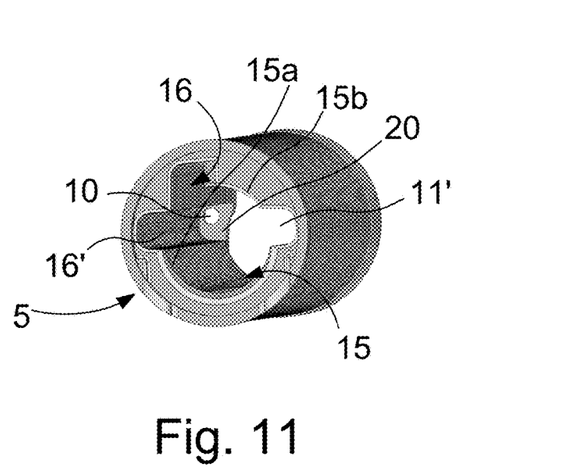
FIG. 11 presents a perspective distal end view of the bending section body of FIG. 10 showing the central passage.
Figure 12A:
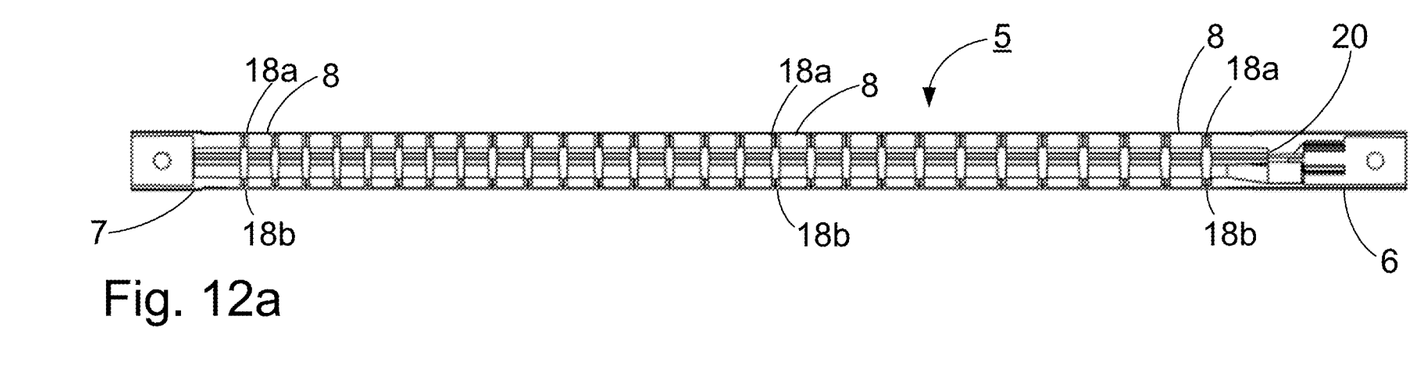
FIG. 12a shows a longitudinal cross-section taken in the plane S of the bending section body of FIG. 9.
Figure 12B:
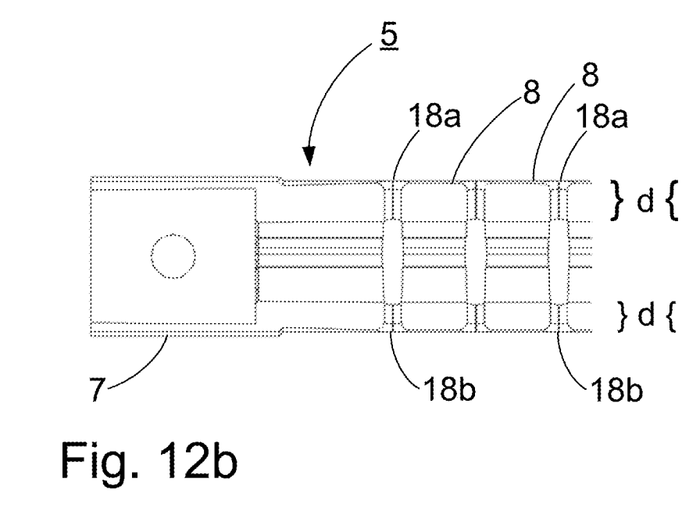
FIG. 12b shows a detailed view of the distal end of the longitudinal cross-section at the left-hand side of FIG. 12a, FIG. 12c shows a detailed view of the proximal end of the longitudinal cross-section at the right-hand side of FIG. 12a, FIG. 13 shows a longitudinal cross-section in isometric view of the bending section body of FIG. 9.
Figure 12C:
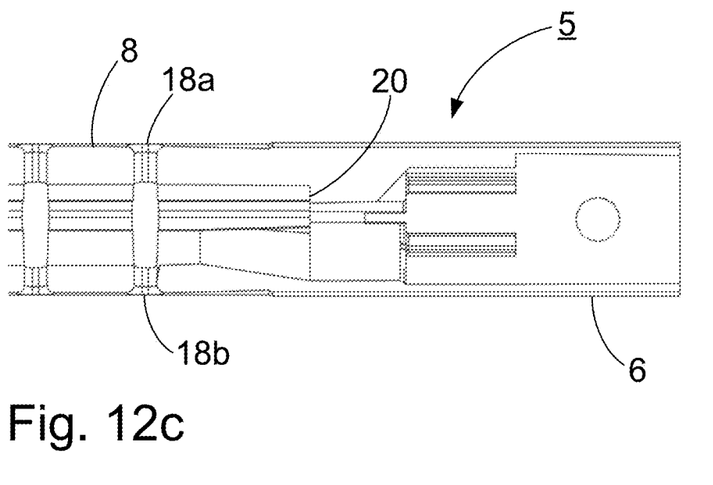
Figure 13:
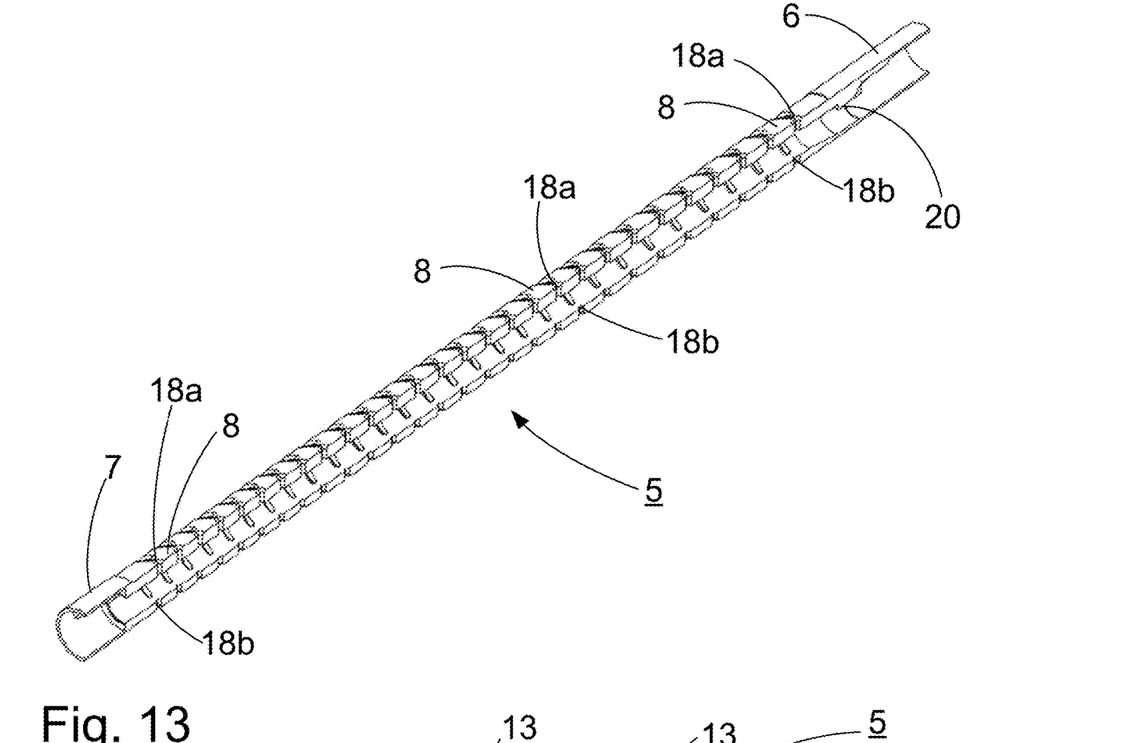
Figure 14:
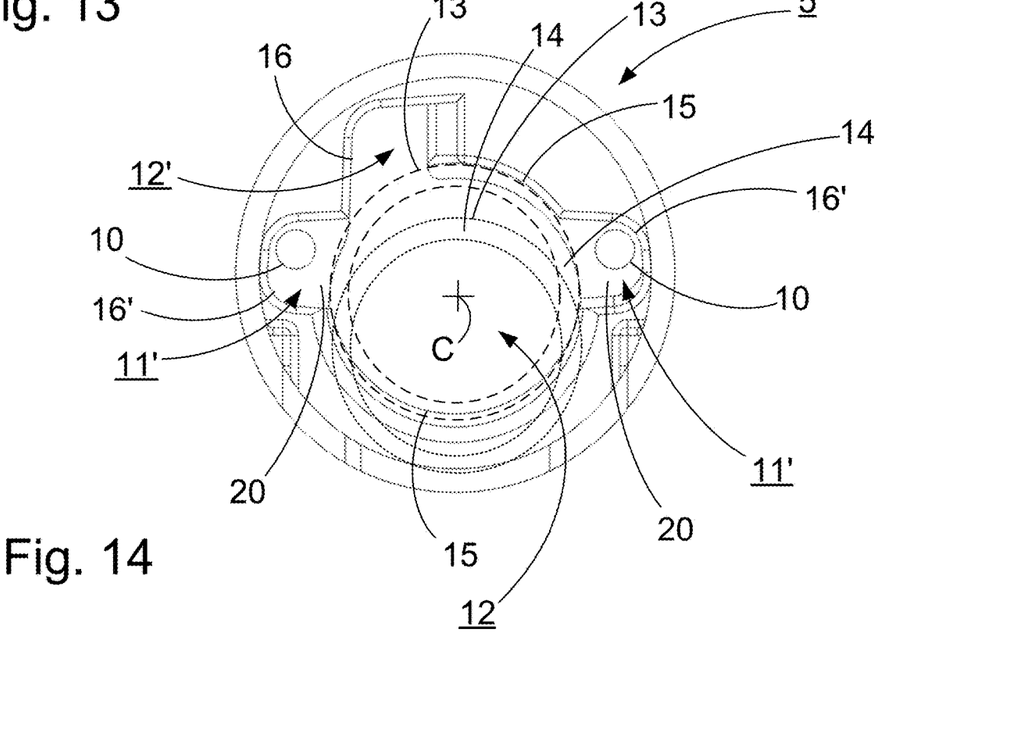
FIG. 14 shows a distal end view of the bending section body of FIG. 9.

The lobe sector may be symmetrical about the longitudinal bending plane, as shown in FIGS. 5 to 8 and 15. The lobe sector may be asymmetrical about the longitudinal bending plane (differently sized/shaped portions on either side of the transverse wall relative to the longitudinal bending plane) or may be positioned on one side of the bending plane, as shown in FIGS. 10, 11, and 14.

Figure 2:
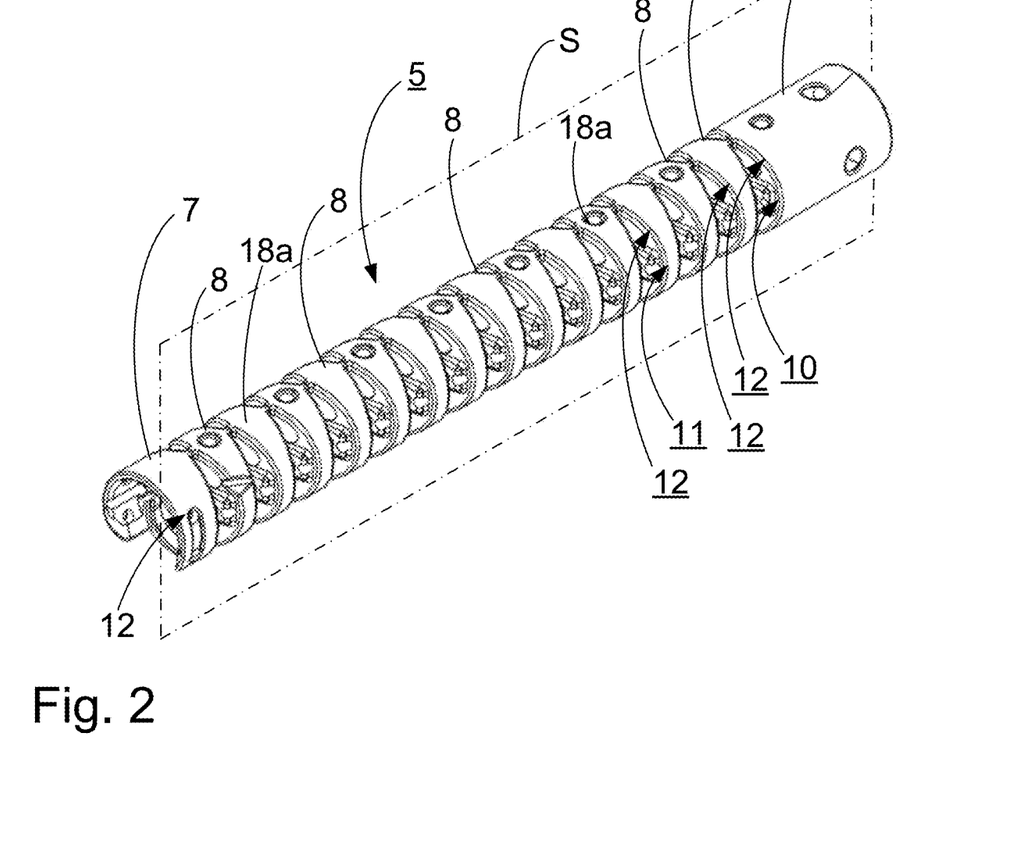
FIG. 2 shows a first embodiment of a bending section body in isometric view.
Figure 3A:
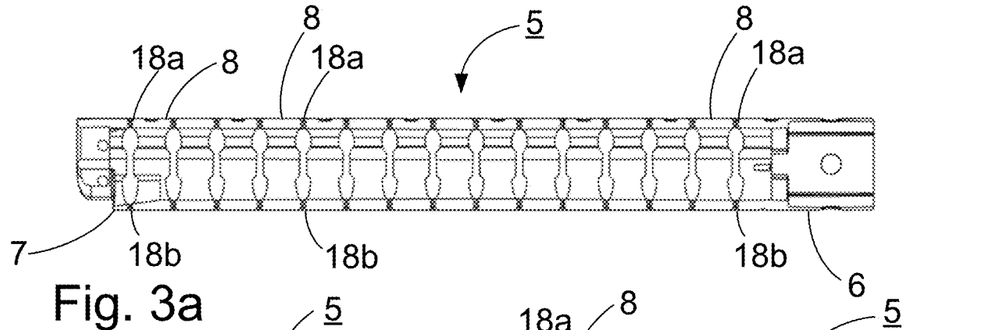
FIG. 3a shows a longitudinal cross-section taken in the plane S of the bending section body of FIG. 2.
Figure 3B:
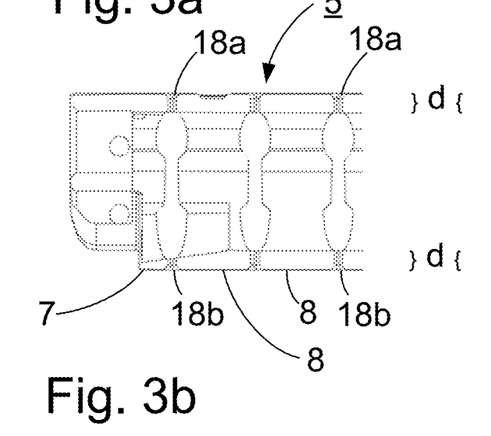
FIG. 3b shows a detailed view of the distal end of the longitudinal cross-section at the left-hand side of FIG. 3a, FIG. 3c shows a detailed view of the proximal end of the longitudinal cross-section at the right-hand side of FIG. 3a, FIG. 4 shows a longitudinal cross-section in isometric view of the bending section body of FIG. 2.
Figure 3C:
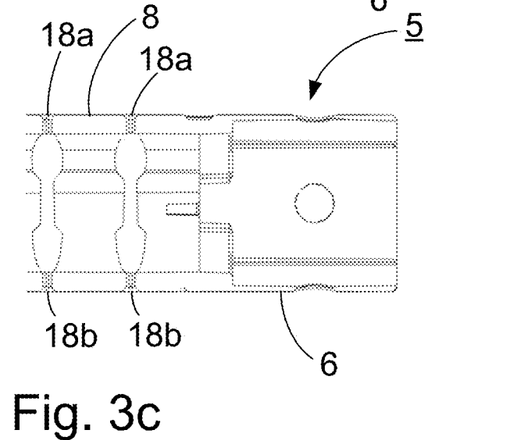
Figure 4:
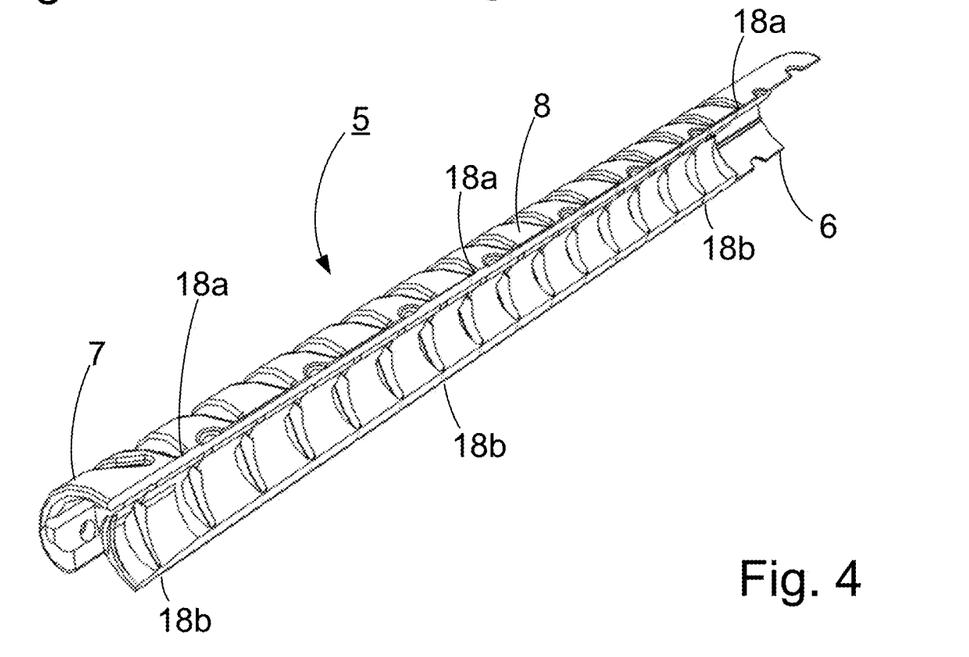

In FIG. 2 a first embodiment of the bending section body 5 is shown. The bending section body comprises a number of articulated segments, including the proximal end segment 6, distal end segment 7, and the number of intermediate segments 8. The segments are preferably molded together with hinge members connecting the segments to each other. If the number of intermediate segments is larger than one, the intermediate segments 8 are preferably identical to each other. However, it is not excluded that gradual changes or other differences exist between segments along the length of the bending section body. The distal end segment 7 is adapted for being connected to a distal tip part accommodating one or more image capture devices, illumination devices, and other electronics. The distal end segment 7 or the distal tip part are often adapted for attachment of the distal ends of pull-wires 22 of a Bowden cable (shown in FIG. 15). The proximal end segment 6 on the other hand is adapted for connection to the remainder of the insertion tube 3. The remainder of the insertion tube 3 may be provided in various embodiments and variants. One typical embodiment may comprise a tightly wound steel coil, covered in a braided layer and an outer water and airtight sheath. The proximal end segment 6 furthermore comprises attachment means and/or retaining means for the distal ends of the Bowden cable tubes covering the pull-wires 22 over the distance from the handle 2 through the insertion tube 3 to the bending section. Pull-wire apertures 10 are provided in the proximal end segment 6 allowing the pull-wires to continue through the bending section body 5 to the distal end segment 7. These pull-wire apertures 10 register or are aligned with pull wire apertures 11 in the intermediate segments 8. In FIG. 2 it can also be seen that each intermediate segment 8 as well as the proximal end segment 6 and the distal end segment 7 have the central passage 12. As will be understood from FIG. 5 these central passages 12 preferably comprise identical cross-sections irrespective of whether they are provided in the intermediate segments 8, the proximal end segment 6 or in the distal end segment 7. The segments 6, 7, 8 are connected by the hinges which are constituted by two hinge parts 18a, 18b extending between the segments in the central or bending plane S. The hinge parts 18a, 18b are shown in more detail in FIGS. 3a, 3b, 3c and 4. The pull-wire apertures in the present embodiment are formed by closed openings in the wall 9, meaning that the closed openings do not form part of the peripheries of the central passages 12. In other embodiments, the pull-wire apertures are formed by cut-outs or "open" openings in the wall 9, meaning that the openings form part of the peripheries of the central passages 12.

As will now be explained in conjunction with FIG. 5 the central passages 12 are adapted in cross-sectional shape to receive and support the exterior surface 13 of the bendable tubular member, or bendable tube, 14 (indicated with dashed lines) providing a working channel 14' of the endoscope 1, the working channel being the inner lumen of the bendable tubular member 14. As can be seen, the tubular member has a circular cross-section, so that when the bendable tubular member 14 is not bent it has a cylindrical exterior surface 13. The lobe 16 and the bendable tube support sector, or cross-sectional shape, 15, are preferably provided along the entire length of a segment 8, or at least along a majority thereof.

Figure 5:
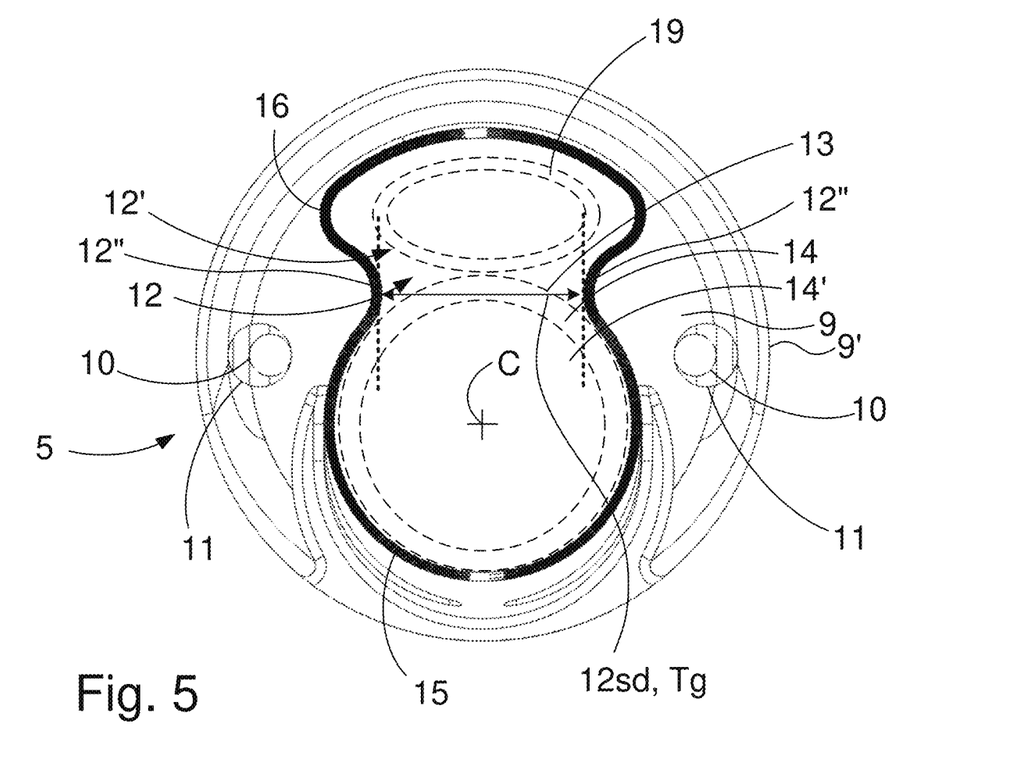
FIG. 5 presents a distal end view of the bending section body of FIG. 2, showing the central passage with a cross-section shape including a bendable tube support sector connected to a lobe sector.

The central passage 12 has a cross-section with a cross-sectional shape which over a large part is a circular sector 15 with a shared center C, in the illustrated example of FIG. 5 comprising a single circle sector, or bendable tube support sector, of roughly 270 degrees, and thus receives and supports the exterior surface 13 of the bendable tube 14 over a corresponding part of the circumference. That is to say, at least when bending, the exterior surface 13 of bendable tube 14 engages the edge of the wall 9 forming the central passage 12 provided by the circular cross-sectional shape 15. This prevents deformation of the bendable tube 14 in any outward direction from the center C along the circular sector. Thus, even during bending of the bending section 5, the engagement between the two prevents deformation of the bendable tubular member 14, i.e. supports the bendable tubular member 14 against kinking. The bendable tube support sector 15 may comprise a single sector formed by arcuate sections with lengths extending at least 220 degrees, preferably about 270 degrees. In other embodiments, the bendable tube support sector 15 may comprise two or more sectors, all with a common center C.

At the non-circular part of the cross-section the lobe 16 extends from the circle. This lobe 16 provides, together with the exterior surface 13 of the bendable tube 14, a circumferentially closed lumen 12' adjacent the working channel. The lobe 16 and circular cross-sectional shape 15 are preferably provided along the entire length of a segment 8, or at least along a majority thereof. The central passage 12 is thus provided through the segment 8. Since no partitioning wall needs to be provided in the bending section body 5 itself between the bendable tubular member 14 forming the working channel and the closed lumen 12', space is saved and more room is provided for the working channel, which may then be made wider, as well as for the electrical cables 17, light fibers etc. Plenty of space is also available for apertures 11 for the pull-wires 22 through the wall 9 of the intermediate segments and similarly for the apertures 10 for the pull-wires 22 through the proximal end segment 6.

The same applies between the segments 6, 7, 8 where the hinges which are constituted by two hinge parts 18a, 18b. That is to say the hinge parts 18a, 18b have an extension in the diametrical direction corresponding to the wall thickness of between the lobe 16 and the imaginary exterior envelope of the generally cylindrical bending section body 5 in the central plane S, and between the circular segment part 15 and the imaginary exterior envelope of the generally cylindrical bending section body 5 also in the central plane S. The hinge parts 18a, 18b are foil hinges meaning short bendable bridges of material between adjacent segments 6, 7 or 8. Width in this respect meaning extension in the vertical direction of FIG. 5, length meaning extension perpendicular to the plane of the drawing in FIG. 5 and thickness meaning extension in the horizontal direction of FIG. 5. By not having any partitioning wall, and accordingly no central hinge part corresponding thereto, allows the width d (as indicated between FIGS. 3b, 3c and 7b, 7c) of the hinge parts 18a and 18b located in the periphery to be made wider than in the prior art, and thereby provide more strength against torsional forces.

Figure 7:
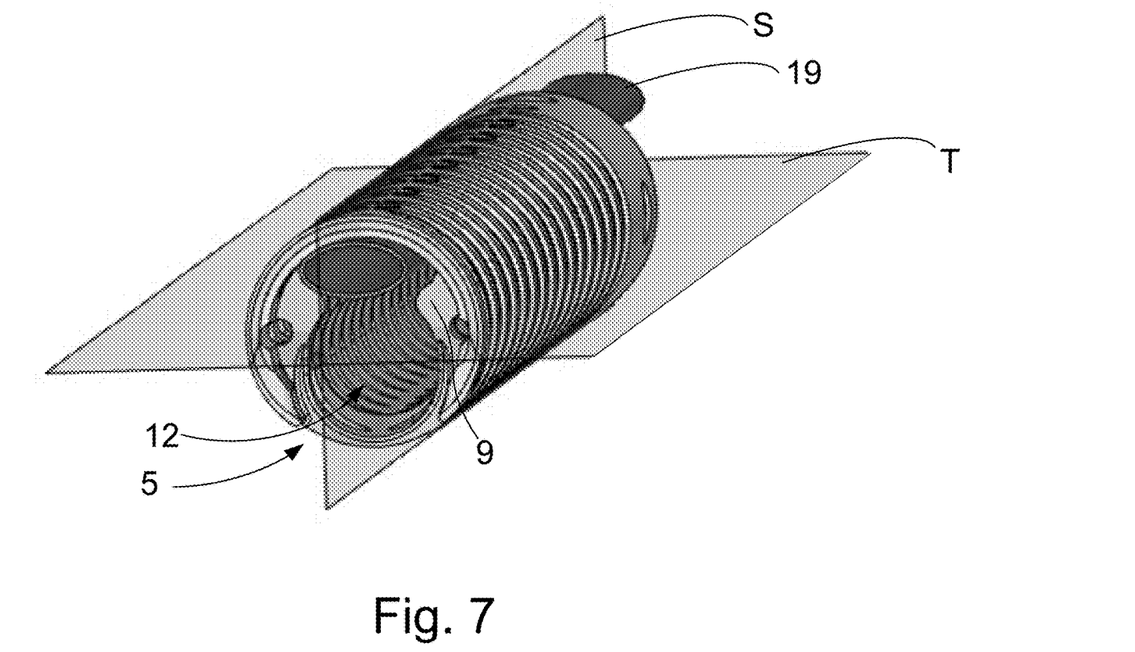
FIG. 7 presents a perspective distal end view of the bending section body of FIG. 5 showing the central passage with a tube extending through the lobe sector.

Although the closed lumen 12' may accommodate the electrical cables 17, illumination light fibers, etc. directly, it is of course not excluded that they may be accommodated in one or more separate conduits 19 (shown in FIGS. 5 and 7). This allows good control of individual cables 17, illumination light fibers etc. in particular in the bending zoned formed by gaps between the individual segments 6, 7, 8. Using such a conduit filled with cables 17, illumination light fibers etc. may furthermore provide some resistance to kinking of the tubular member 14 between segments 6, 7, 8 and any tendency for the tubular member 14 to squeeze into the lobe 16 reducing the lumen 12'.

Figure 6:
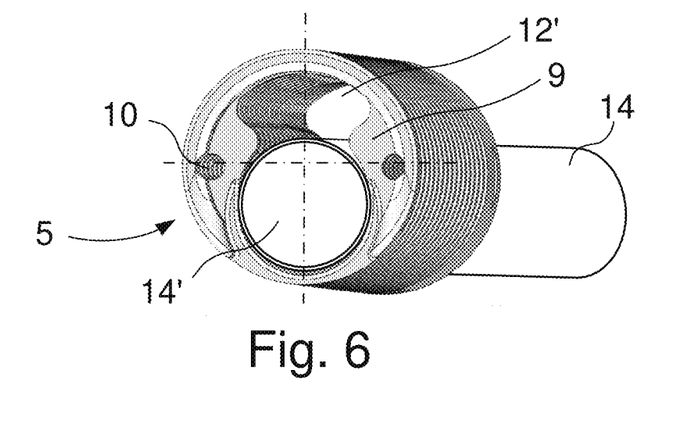
FIG. 6 presents a perspective distal end view of the bending section body of FIG. 5 showing the central passage with a bendable tube extending through the bendable tube support sector.
Figure 8:
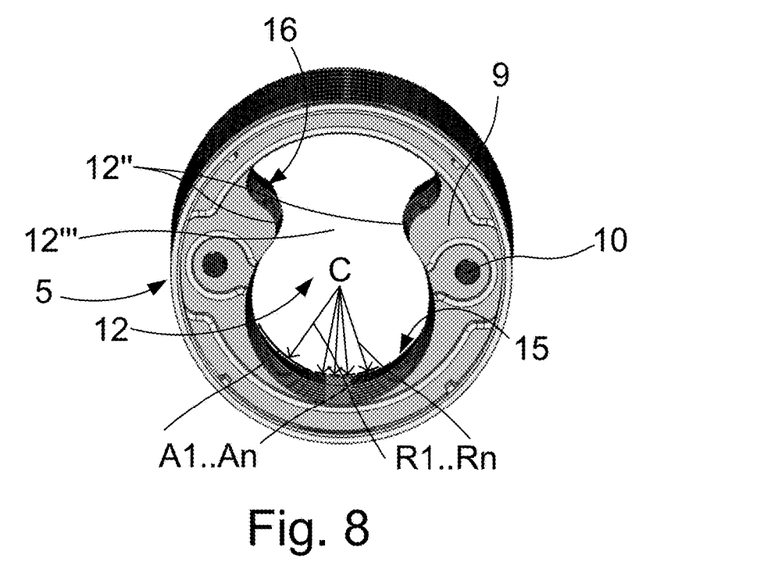
FIG. 8 presents a slightly perspective proximal end view of the bending section body of FIG. 5.

FIGS. 6 to 8 provide additional views of the bending section body 5 depicted in FIG. 5. FIG. 6 illustrates the placement of the bendable tube 14. The wall 9 comprises opposite protrusions 12'' defining a gap 12''' intermediate the bendable tube support sector 15 and the lobe sector 16. The gap 12''' is formed between opposite surfaces of the periphery of the central passage. A shortest distance 12sd of the gap is shown in FIG. 5, which as shown occurs between parallel lines tangential, at the gap, to the periphery of the central passage. A plane passing thorugh the line denoting the shortest distance, denoted as Tg in FIG. 5 is also shown. As shown, the plane Tg does not traverse the pull-wire apertures 11. FIG. 5 also shows an outer periphery 9' of the wall'. The central passage is devoid of material across the gap, such that the space defined by the bendable tube support sector along a plane traversing the wall is contiguous with the space defined by the lobe sector along said plane.

FIG. 7 shows the conduit 19 and a transverse plane T perpendicular to the longitudinal bending plane S. In the present embodiment the pull-wire apertures 11 are traversed by the transverse plane T but that is not necessarily the case in other embodiments in which the pull-wire apertures 11 are placed asymmetrically relative the bending plane S. FIG. 8 illustrates a proximal view of the bending section body 5. The periphery of the bendable tube support sector 15 comprises a plurality of contiguous arcs A1.. An having a common center C and radii R1..Rn. If the bendable tube support sector has two or more sectors, each sector comprises contiguous arcs, however the two or more sectors will not be contiguous.

Figure 9:
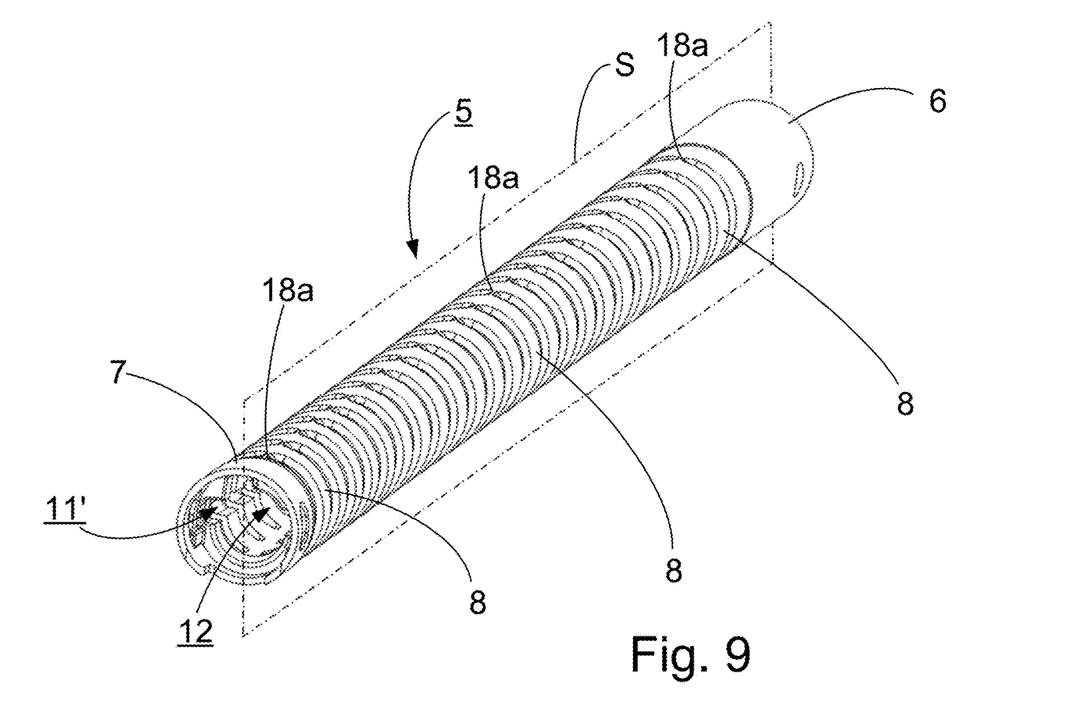
FIG. 9 shows a second embodiment of a bending section body in isometric view.

Turning now to FIG. 9, a second embodiment of the bending section body 5 is shown in isometric view. For ease of understanding the same reference numerals are used for the same features as in the first embodiment. FIGS. 10 and 11 provide additional views of the bending section body 5 depicted in FIG. 9. FIG. 10 illustrates the placement of the bendable tube 14. In the present embodiment the pull-wire apertures, denoted as passages 11' formed by lobes 16', are "open" and are placed symmetrically relative the bending plane S. The bendable tube support sector 15 comprises arcuate sections with lengths extending at least 220 degrees, preferably about 270 degrees, denoted by sections 15a and 15b.

Like the first embodiment the bending section body 5 of the second embodiment is preferably integrally molded as one single-piece item in a suitable molding process, such as injection molding. The bending section body comprises a number of articulated segments, including a proximal end segment 6 distal end segment 7 and a number of intermediate segments 8. As will be noticed the number of intermediate segments 8 is higher than in the first embodiment. In the specific embodiment depicted in FIG. 9 the number of intermediate segments is twenty-seven wherein in the first embodiment depicted in FIG. 2 it is only about half that number, namely fourteen. The exact number of intermediate segments is however not of importance to any of the specific embodiments depicted and may be varied, depending on purpose of the endoscope, the dimension of the endoscope or the like. The intermediate segments 8 are also in the second embodiment preferably identical to each other. The distal end segment 7 is adapted to accommodate one or more image capture devices, illumination devices, and other electronics. The distal end segment 7 is also adapted for attachment of the distal ends of pull-wires 22 of a Bowden cable. The proximal end segment 6 on the other hand is adapted for connection to the remainder of the insertion tube 3. The proximal end segment 6 furthermore comprises attachment means and/or retaining means for the distal ends of the Bowden cable tubes covering the pull-wires 22 over the distance from the handle 2 through the insertion tube 3 to the bending section. These retaining means include at least one transversal wall 20 of a given thickness arranged within the proximal end segment 6. Pull-wire apertures 10 are provided at this transversal wall 20 in the proximal end segment 6 allowing the pull-wires to continue through the bending section body 5 to the distal end segments 7.

Unlike the first embodiment the intermediate segments 8 do not comprise apertures for the pull-wires. Instead, as can best be seen in FIG. 14, passages 11' are formed by lobes 16' on the generally circular cross section of the central passage 12 in each intermediate segment. In the unbent state of the bending section body 5, all passages 11' preferably match in position or are aligned with pull-wire apertures 10 in the transversal wall 20 the proximal end segment 6, and at least the passages 11' in the intermediate segment 8 adjacent the proximal end segment 6 are aligned or otherwise match in position. As can best be seen from FIGS. 11 and 14, the wall 20 is provided within the proximal end segment, by making a slight off-set of the central passage 12 away from the center axis towards the periphery of the proximal end segment 6. The tubular member 14 forming the working channel in the assembled endoscope 1 thus follows a slight s-curve through the bending section body 5, as illustrated with the dotted outline in FIG. 14. Thereby, sufficient material thickness is provided to withstand the forces occurring where the outer tubes of the Bowden cables terminate within the proximal end segment 6.

As can also be seen from FIG. 14, the lobe 16, adapted to accommodate the electrical cables, illumination light fibers, etc., is also provided. This lobe 16 thus essentially serves the same function as the lobe 16 of the first embodiment. However, in order to increase the space available for the cylindrical part of the central passage it has been off-set with respect to the bending plane, so that the width of the hinge parts are not restricted by anything else than the outer diameter of imaginary envelope of the bending sector body 5 and the outer diameter of the tubular member 14 corresponding to the diameter of the circular sector parts of the cross-section of the central passage 12 adapted to receive and support the exterior surface of the tubular member 14.

The second embodiment thus comprises a central passage 12 with a cross-section comprising two circular sectors 15 with the shared center C and the same radius and three lobes 16, 16', the three lobes 16 forming together with the exterior wall of the tubular member closed lumens for pull-wires 22 on one hand and electrical cables, illumination light fibers etc. on the other hand. The two circular sectors 15 make up the majority of the circumference of the central passage 12 supporting the tubular member 14, i.e. more than 180 degrees.

Figure 15:
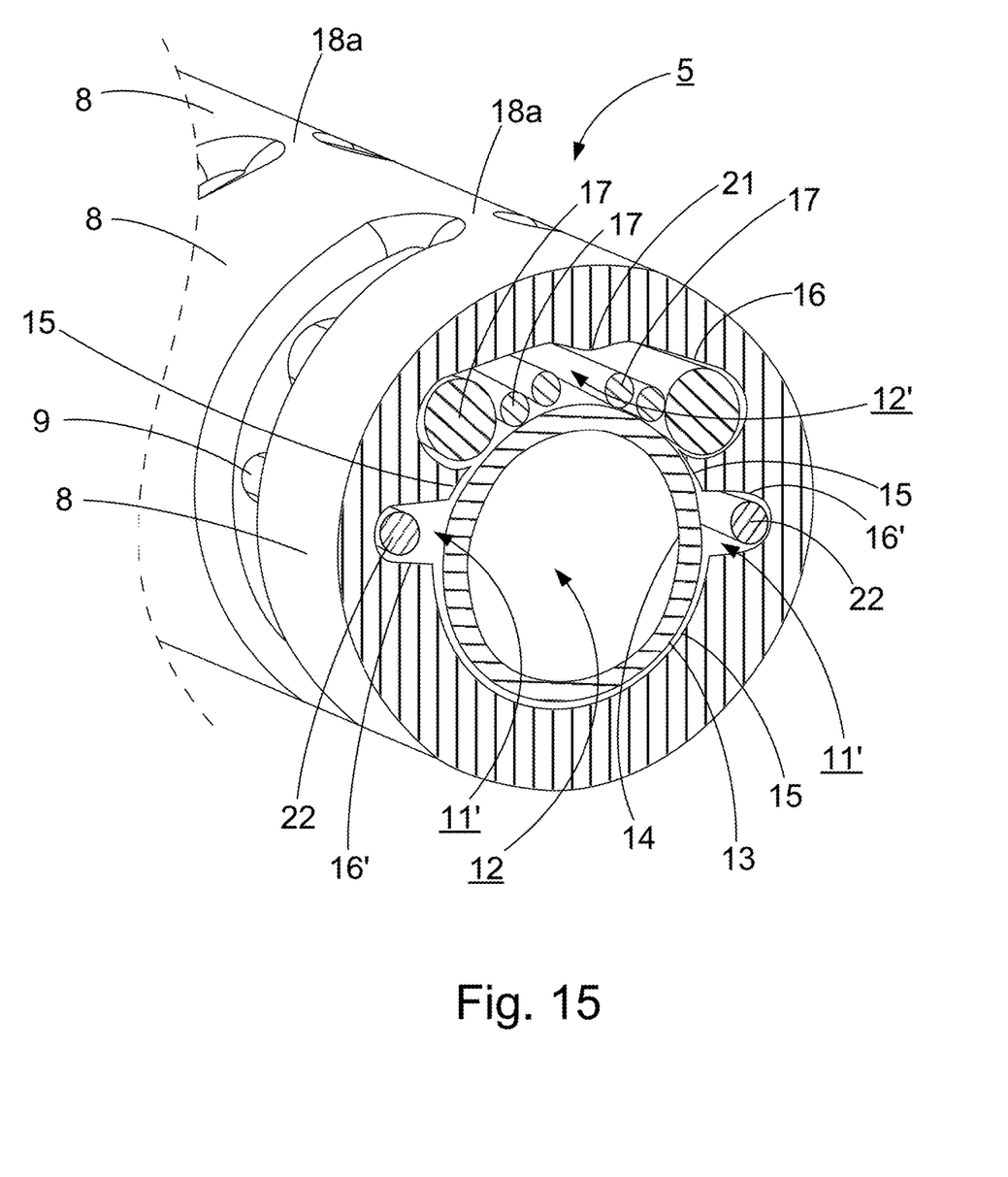
FIG. 15 shows a cross-section through an intermediate segment of a third embodiment with the working channel tube, pull-wire and electrical wires in place.

Turning now to FIG. 15, a third embodiment of the bending section body is shown. In essence, only the cross-section of the central passage differs from the other embodiments incorporating features of the cross-section from both of them. As for the rest of the features of the bending section body 5 the skilled person will understand that they may correspond to any of the other embodiment, e.g. regarding length, diameter, number of intermediate segments, details of proximal end segment and distal end segment, etc. Likewise, such details may be interchangeable between the first and second embodiments too.

As will be seen this third embodiment exhibits mirror symmetry as does the first embodiment. Thus, rather than the lateral off-set of the lobe 16 in the second embodiment, the lobe 16 is symmetrical about the central, bending, plane with a narrow part in the middle which aligns with the hinge part 18a. The narrow part which is provided by an inward rib 21 could be made higher than shown, and in fact extend all the way down to abutment with the exterior of the tubular member 14, thus splitting the lobe 16 in two and adding further support to the tubular member 14. Two closed lumens for electrical cables 17, illumination light fibers etc. would then be formed. Similar to the second embodiment a pair of lobes 16' are provided, whereby the inner wall of the bending section segment 8, together with the exterior surface of the tubular member 14, form closed lumens for the pull-wires 22. As can be seen, there are three circular sectors 15 with the same radius and the shared center C in this embodiment, still totaling more than 180 degrees for good support of the tubular member 14. Ideally, the exterior surface 13 of the tubular member 14 abut the entire length of the three circular sectors 15, but for illustration purposes small gaps are shown in FIG. 15 and some of the other figures. If the rib 21 was to be extended to also receive and support the tubular member, it too could be shaped to provide a fourth circular sector, also with the same shared center C and the same radius.

Additional examples and variations of the foregoing embodiments:

Item 1. An endoscope comprising an articulated bending section body, said articulated bending section body comprising a number of segments including a proximal end segment, a distal end segment and a number of intermediate segments arranged between the proximal segment and the distal segment, where a pair of end hinge members is provided between the proximal end segment and one of said intermediate segments, where a pair of end hinge members is provided between the distal end segment and one of said intermediate segments, and where a pair of intermediate hinge members is provided between any adjacent intermediate segments, at least some of said intermediate hinge members defining a longitudinal central plane of said articulated bending section body, where each intermediate segment has a central passage adapted in cross-sectional shape to receive and support the exterior surface of a bendable tubular member providing a working channel of the endoscope against outward deformation, where the cross-sectional shape comprises a number of sectors of a circular periphery having a shared center and the same radius, the total length of said sectors being longer than half of said circular periphery, so as to provide said support for the exterior of the bendable tubular member providing the working channel of the endoscope, and where said cross-sectional shape comprises at least one outwardly extending lobe, wherein the exterior of the bendable tubular member providing the working channel of the endoscope forms a closed lumen adjacent but separated from the working channel of the endoscope.

Item 2. An endoscope according to item 1, wherein said intermediate segments are symmetrical about said longitudinal central plane.

Item 3. An endoscope according to item 1, wherein said shared center lies in the longitudinal central plane and said at least one lobe is arranged asymmetrical with respect to said longitudinal central plane.

Item 4. An endoscope according to any one of the preceding items wherein a pair of lobes are arranged symmetrically about said longitudinal central plane, and wherein pull wires are arranged in the closed lumens formed adjacent but separated from the working channel of the endoscope.

Item 5. An endoscope according to any one of the preceding items wherein a cable conduit is accommodated in said closed lumen.

Item 6. An endoscope according to any one of the preceding items, wherein the tubular member delimits the pull wire aperture thereby keeping the pull wire in the pull wire aperture.

Item 7. An endoscope according to any one of the preceding items, wherein an outer diameter of the articulated bending section is below 3.0 mm, preferably below 2.8 mm.

Item 8. An endoscope according to item 7, wherein an inner diameter of the working channel is least 1.2 mm, preferably at least 1.3 mm.

Item 9. A system comprising a display unit and an endoscope according to any one of the preceding items connectable to said display unit.

Although the above description has been given based on an endoscope bendable in a single plane only, i.e. perpendicular to the plane of the hinge parts 18a, 18b, the skilled person will understand that the same principles of providing closed lumens by using the tubular member 14, would also be applicable to an endoscope 1 bendable in two planes. That is to say, where the bending section comprises two sets of hinge parts arranged in two planes, preferably perpendicular to each other.

Reference numerals used:
1 Endoscope
2 Handle
3 Insertion tube
4 Bending section
5 Bending section body
6 Proximal end segment
7 Distal end segment
8 Intermediate segments
9 Transverse wall
10 Pull-wire apertures
11, 11' Pull-wire apertures
12 Central passage
12' Central passage lumen
13 Exterior surface of tubular member
14 Tubular member
15 Circular sector
16, 16' Lobe
17 Electrical cables
18a Hinge part
18b Hinge part
19 Conduit
20 Transversal wall
21 Inward rib
22 Pull-wires
100 Display device
101 Cable or wireless connection

I claim:

1. An endoscope comprising: a bending section body including:
    segments including a proximal end segment, a distal end segment and intermediate segments arranged between the proximal end segment and the distal end segment, and hinges connecting adjacent of the segments, the bending section body being a single-piece item comprising the hinges and the segments,
    wherein each intermediate segment has a transverse wall having a central passage with a cross-section shape comprising a bendable tube support sector adjacent to a lobe sector, the bendable tube support sector having a periphery, the lobe sector having a periphery, the transverse wall comprising a pull-wire aperture and opposite protrusions creating a gap, the gap being between the bendable tube support sector and the lobe sector, a solid portion of the wall extending from an outer periphery of the wall to the bendable tube support sector comprising the pull-wire aperture, wherein a transverse plane passing through a shortest distance between the opposite protrusions does not traverse the pull-wire aperture, and
    wherein the periphery of the bendable tube support sector has a length and is sized and shaped to receive a bendable tube having an outer circumference and providing a working channel of the endoscope, the length of the periphery of the bendable tube support sector being longer than half of the outer circumference of the bendable tube so as to support the bendable tube against outward deformation.

2. The endoscope of claim 1, further comprising the bendable tube, wherein the bendable tube has a diameter, and wherein the gap is smaller than the diameter.

3. The endoscope of claim 1, wherein a longitudinal bending plane traverses at least some of the hinges and the bending section body bends along the longitudinal bending plane, and wherein the longitudinal bending plane traverses the bendable tube support sector and the lobe sector.

4. The endoscope of claim 3, wherein the transverse wall further comprises a second pull-wire aperture arranged symmetrically with the pull-wire aperture about the longitudinal bending plane, further comprising pull-wires passing through the pull-wire apertures.

5. The endoscope of claim 4, further comprising the bendable tube, wherein the pull-wire aperture and the second pull-wire aperture are formed by lobes connected to the periphery of the bendable tube support sector, wherein, after assembly, the bendable tube delimits the pull-wire apertures thereby keeping the pull-wires in the pull-wire apertures.

6. The endoscope of claim 3, wherein the intermediate segments are symmetrical about the longitudinal bending plane.

7. The endoscope of claim 1, wherein the periphery of the bendable tube support sector is comprised of a plurality of contiguous arcs having a common center.

8. The endoscope of claim 7, wherein the common center lies in the longitudinal bending plane.

9. The endoscope of claim 7, wherein the plurality of contiguous arcs have a common radius.

10. The endoscope of claim 1, wherein a longitudinal bending plane traverses at least some of the hinges and the bending section body bends along the longitudinal bending plane, and wherein the lobe sector is arranged asymmetrical with respect to the longitudinal bending plane.

11. The endoscope of claim 1, wherein a longitudinal bending plane traverses at least some of the hinges and the bending section body bends along the longitudinal bending plane, and wherein the lobe sector is positioned entirely on one side of the transverse wall relative to the longitudinal bending plane.

12. The endoscope of claim 1, further comprising a cable conduit accommodated in the lobe sector.

13. The endoscope of claim 1, wherein an outer diameter of the bending section body is less than 3.0 mm.

14. The endoscope of claim 13, wherein an inner diameter of the working channel is at least 1.2 mm.

15. A system comprising a display unit and the endoscope according of claim 1, wherein the endoscope is connectable to the display unit.

16. The endoscope of claim 1, wherein the bending section body further comprises a different segment located between the proximal end segment and the distal end segment, the different segment being different than at least one of the intermediate segments.

17. The endoscope of claim 1, further comprising the bendable tube, wherein the bendable tube has a diameter, the gap is smaller than the diameter, the periphery of the bendable tube support sector is comprised by one contiguous arc, the periphery of the lobe sector is comprised by one contiguous arc, an outer diameter of the bending section body is less than 3.0 mm and an inner diameter of the bendable tube is at least 1.2 mm.

18. The endoscope of claim 1, further comprising the bendable tube, wherein the bendable tube has a diameter, the gap is smaller than the diameter, the periphery of the bendable tube support sector is comprised by one contiguous arc, an outer diameter of the bending section body is less than 3.0 mm and an inner diameter of the bendable tube is at least 1.2 mm.

19. A bending section body for an endoscope, the bending section body comprising:
    segments including a proximal end segment, a distal end segment and intermediate segments arranged between the proximal end segment and the distal end segment, and hinges connecting adjacent of the segments, the bending section body being a single-piece item comprising the hinges and the segments,
    wherein each intermediate segment has a transverse wall having a central passage with a cross-section shape comprising a bendable tube support sector adjacent to a lobe sector, the bendable tube support sector having a periphery, the lobe sector having a periphery, the transverse wall comprising a pull-wire aperture and opposite protrusions creating a gap, the gap being between the bendable tube support sector and the lobe sector, a solid portion of the wall extending from an outer periphery of the wall to the bendable tube support sector comprising the pull-wire aperture, wherein a transverse plane passing through a shortest distance between the opposite protrusions does not traverse the pull-wire aperture, and
    wherein the periphery of the bendable tube support sector has a length and is sized and shaped to receive a bendable tube having an outer circumference and providing a working channel of the endoscope, the length of the periphery of the bendable tube support sector being longer than half of the outer circumference of the bendable tube so as to support the bendable tube against outward deformation.

20. The endoscope of claim 16, wherein the intermediate segments are identical.

* * * * *